(12) United States Patent
Bennetzen et al.

(10) Patent No.: US 8,445,746 B2
(45) Date of Patent: May 21, 2013

(54) COMPOSITIONS AND METHODS FOR IDENTIFYING GENETIC SEQUENCES WITH TOXIN RESISTANCE IN PLANTS

(75) Inventors: Jeffrey L. Bennetzen, Bogart, GA (US); Ervin D. Nagy, O'Fallon, MO (US)

(73) Assignee: University of Georgia Research Foundation, Inc., Athens, GA (US)

( * ) Notice: Subject to any disclaimer, the term of this patent is extended or adjusted under 35 U.S.C. 154(b) by 475 days.

(21) Appl. No.: 12/528,290

(22) PCT Filed: Feb. 25, 2008

(86) PCT No.: PCT/US2008/002417
§ 371 (c)(1),
(2), (4) Date: Mar. 16, 2010

(87) PCT Pub. No.: WO2008/103482
PCT Pub. Date: Aug. 28, 2008

(65) Prior Publication Data
US 2010/0279287 A1  Nov. 4, 2010

Related U.S. Application Data

(60) Provisional application No. 60/986,097, filed on Nov. 7, 2007, provisional application No. 60/891,302, filed on Feb. 23, 2007.

(51) Int. Cl.
*A01H 1/02* (2006.01)
*A01H 1/04* (2006.01)
*C12Q 1/68* (2006.01)
*C07H 21/04* (2006.01)

(52) U.S. Cl.
USPC .......... 800/267; 800/298; 800/301; 435/6.11; 435/6.13; 536/23.6

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,769,061 A | 9/1988 | Comai | |
| 4,810,648 A | 3/1989 | Stalker | |
| 4,940,835 A | 7/1990 | Shah et al. | |
| 4,975,374 A | 12/1990 | Goodman et al. | |
| 5,266,317 A | 11/1993 | Tomalski et al. | |
| 5,580,852 A | 12/1996 | Putnam et al. | |
| 5,607,914 A | 3/1997 | Rao et al. | |
| 5,659,026 A | 8/1997 | Baszczynski et al. | |
| 5,683,439 A | 11/1997 | Jensen | |
| 5,689,049 A | 11/1997 | Cigan et al. | |
| 5,689,051 A | 11/1997 | Cigan et al. | |
| 2004/0237137 A1* | 11/2004 | Osumi et al. | 800/279 |

FOREIGN PATENT DOCUMENTS

| | | |
|---|---|---|
| EP | 0 242 246 | 10/1987 |
| EP | 0 333 033 | 9/1989 |
| WO | WO 93/02197 | 2/1993 |
| WO | WO 94/00992 | 1/1994 |
| WO | WO 99/25821 | 5/1999 |

OTHER PUBLICATIONS

Keskin et al. Protein Science, 13:1043-1055, 2004.*
Guo et al. PNAS, 101: 9205-9210, 2004.*
Rabinowicz,P.D et al. Accession No. BZ347009; 2002.*
Abe et al. (1987) J. Biol. Chem. 262:16793 (nucleotide sequence of rice cysteine proteinase inhibitor).
Altschul et al. (1990) J. Mol. Biol. 215:403-410.
An et al. (1989) Plant Cell 1 :115-122.
Beachy et al. (1990) Ann. Rev. Phytopathol. 28:451.
Beaucage and Caruthers (1981) Tetra. Lefts. 22(20): 1859-1862.
Bevan et al. (1984) Nucleic Acids Res. 12:8711-8721.
Bidney et al. (1992) Plant Mol. Biol. 18:301-313.
Botella et al. (1994) Plant Mol. Biol. 24:757.
Bretagne-Sagnard et al. (1996) Transgenic Res. 5:131-137.
Brown et al. (1979) Meth. Enzymol. 68:109-151.
Bullock et al. (1987) BioTechniques 5:376-378.
Chiu et al. (1996) Current Biology 6:325-330.
Christensen et al. (1992) Plant Mol. Biol. 18:675-689.
Christou et al. (1987) Proc. Natl. Acad. Sci. USA 84:3962.
D' Halluin et al. (1992) Plant Cell 4:1495-1505.
DeBlock et al. (1981) EMBO J. 6:2513-2518.
De Greef et al. (1989) Bio/Technology 7:61.
Dennis et al. (1984) Nucleic Acid Res. 12:3983-3990.
Deshayes et al. (1985) EMBO J. 4:2731.
Draper et al. (1982) Plant Cell Physiol. 23:451.
Elliot et al. (1993) Plant Mol. Biol. 21:515 (nucleotide sequences of tomato invertase genes).
Ewing, B., L. Hillier, M. Wendl, P. Green, Genome Res. 8, 175 (1998).
Fisher et al. (1993) Plant Physiol. 102:1045 (maize endosperm starch branching enzyme II).
Gallie et al. (1987) Nucleic Acids Res. 15:3257-3273.
Gardner et al. (1981) Nucleic Acid Res. 9:2871-2888.
Gatz et al. (1994) Mol. Gen. Genet. 243:32-38.
Geiser et al. (1986) Gene 48:109.
Goff, et al. (1990) EMBO J. 9:2517-2522.
Gordon, D., C. Abajian, P. Green, Genome Res. 8,195 (1998).
Griess et al. (1994) Plant Physiol. 104:1467.
Guerineau et al. (1990) Plant Mol. Bio. 15:127-136.
Guerrero et al. (1990) Mol. Gen. Genet. 224:161-168.
Hammock et al. (1990) Nature 344:458.

(Continued)

*Primary Examiner* — Medina A Ibrahim
(74) *Attorney, Agent, or Firm* — Davis Wright Tremaine LLP

(57) ABSTRACT

This invention relates generally to useful compositions and methods related to plant site-directed recombination. In particular, the invention relates to novel nucleic acid sequences unique to a portion of the *sorghum* NBS-LRR region, as well as vectors, seeds, plant parts and plants comprising these sequences. Methods to investigate recombination co-factors, and methods to investigate potential herbicides are within the scope. This invention also relates to fungal pathogens of *sorghum*, particularly *Periconia circinata*.

18 Claims, 4 Drawing Sheets

OTHER PUBLICATIONS

Hanahan et al. (1983) J Mol Biol 166:557-580.
Hayes et al. (1992) Biochem. J. 285:173.
Herrera-Estrella et al. (1983) EMBO J. 2:987-992.
Herrera-Estrella et al. (1983) Nature 303:209-213.
Hiei et al. (1994) Plant J. 6:271-282.
Higgins et al. (1988) Gene 73:237-244.
Higgins, et al., Nucleic Acids Research. pp. 4673-4680, vol. 22, (1994).
Hille et al. (1986) Plant Mol. Biol. 7:171-176.
Horsch, et al. (1985). Science 227:1229-1231.
Huang et al. (1992) Computer Applications in the Biosciences, pp. 155-165, vol. 8(2).
Huub et al. (1993) Plant Mol. Biol. 21:985 (nucleotide sequence of cDNA encoding tobacco proteinase inhibitor I).
Ishida et al. (1996) Nature/Biotechnology 14:745-750.
Jaynes et al. (1993) Plant Sci 89:43.
Jefferson (1987) Plant Mol. Biol. Rep. 5:387.
Jones et al. (1987) Mol. Gen. Genet. 210:86-91.
Jones et al. (1994) Science 266:789 (cloning of the tomato Cf-9 gene for resistance to *Cladospoή um fulvum*).
Kado (1991) Crit. Rev. Plant Sci. 10:1.
Kain et al. (1995) BioTechniques 19:650-655.
Kawalleck et al. (1993) Plant Molec. Biol. 21:673.
Klein et al. (1992) Biotechnology 10:268.
Kloesgen et al. (1986) Mol. Gen. Genet. 203:237-244.
Knutzon et al. (1992) Proc. Natl. Acad. Sci. USA 89:2624.
Kramer et al. (1993) Insect Biochem. Mol. Biol. 23:691.
Kumar, S., K. Tamura, M. Nei, Brief Bioinform 5, 50 (2004).
Lamb et al. (1992) Bio/Technology 10:1436.
Last et al. (1991) Theor. Appl. Genet. 81:581-588.
Laursen, et al. (1994) Plant Mol. Biol. pp. 51-61, vol. 24(1).
Lee et al. (1988) EMBO J. 7:241.
Lepetit et al. (1992) Mol. Gen. Genet. 231:276-285.
Lewis et al., Genome Biol. 3, research 0082.1 (2002).
Linthorst, et al. "Tobacco proteinase inhibitor I genes are locally, but not systematically induced by stress," *Plant Molecular Biology*, pp. 985-992, vol. 21, 1993.
Logemann et al. (1992) Bio/Technology 10:305.
Ludwig et al. (1990) Science 247:449.
Marshall et al. (1992) Theor. Appl. Genet. 83:435.
Martin et al. (1993) Science 262:1432.
McElroy et al. (1990) Plant Cell 2:163-171.
Meijer et al. (1991) Plant Mol. Biol. 16:807-820.
Miki et al. (1990) Theor. Appl. Genet. 80:449.
Miki, et al. 1993. "In: Methods in Plant Molecular Biology and Biotechnology, Glick and Thompson (eds.)." *CRC Press, Inc.: Boca Raton*, pp. 67-88.
Mindrinos et al. (1994) Cell 78:1089.
Murray, M. G., W. F. Thomson (1980) Nucl. Acids Res. 8:4321.
Nagy, et al. "Fine mapping of the Pc locus of *Sorghum bicolor*, a gene controlling the reaction to a fungal pathogen and its host-selective toxin," *Theor Appl Genet*, pp. 961-970, vol. 114, 2007.
Nagy et al. "Pathogen corruption and site-directed recombination at a plant disease resistance gene cluster," *Genome Research*, pp. 1918-1923. vol. 18, 2008.
Nakayama et al. (1992) FEBS Lett 30:167-170.
Narang et al. (1979) Meth. Enzymol. 68:90-99.
Needham-VanDevanter et al. (1984) Nucleic Acids Res. 12:6159-6168.
Needleman and Wunsch (1970) J. Mol. Biol. 48:443.
Neuhaus et al. (1987) Theor. Appl. Genet. 75:30-36.
Odell et al. (1985) Nature 313:810-812.
Palmer et al. (1994) Gene 143:7-8.
Pang et al. (1992) Gene 116:165.
Pearson and Lipman (1988) Proc. Natl. Acad. ScL USA 85:2444.
Pen et al. (1992) Bio/Technology 10:292.
Pratt et al. (1989) Biochem. Biophys. Res. Commun. 163:1243.
Przibilla et al. (1991) Plant Cell 3:169.
Raboy et al. (1990) Maydica 35:383.
Reagan (1994) J. Bio. Chem. 269:9.
Reich et al. (1986) Biotechnology 4:1001-1004.
Reina, M., Ponte, I., Guillen, P., Boronat, A. and Palau, J. (1990) Nucleic Acids Res. 18(21):6426.
Sambrook et al. (1989) Molecular Cloning: A Laboratory Manual (2d ed., Cold Spring Harbor Laboratory Press, Plainview, N. Y.).
Sanford (1990) Physiol. Plant. 79:206.
Schena et al. (1991) Proc. Natl. Acad. Sci. USA 88:10421.
Sengupta-Gopalan et al. (1985) Proc. Natl. Acad. Sci. USA 82:3320-3324.
Shah et al. (1986) Science 233:478-481.
Shiroza et al. (1988) J. Bacteriol. 170:810.
Smith and Waterman (1981) Adv. Appl. Math. 2:482.
Søgaard et al. (1993) J. Biol. Chem. 268:22480 (site-directed mutagenesis of barley amylase gene).
Solovyev, et al. (1997) Intel. Syst. Mol Biol., pp. 294-302, vol. 5.
Stalker et al. (1988) Science 242:419-423.
Steinmetz et al. (1985) Mol. Gen. Genet. 200:220 (nucleotide sequence of *Bacillus subtilis* levansucrase gene).
Sumitani et al. (1993) Biosci. Biotech. Biochem. 57:1243 (nucleotide sequence of *Streptomyces mtrosporeus* α-amylase inhibitor).
Tavladoraki et al. (1993) Nature 366:469.
Thompson et al. (1987) EMBO J. 6:2519-2523.
Timko et al. (1985) Nature 318:579-582.
Toubart et al. (1992) Plant J. 2:367.
Twell et al. (1989) Mol. Gen. Genet. 217:240-245.
Twell et al. (1993) Sex. Plant Reprod. 6:217-224.
Van Damme et al. (1994) Plant Mol. Biol. 24:825.
Van Hartingsveldt, et al. (1993) Gene, pp. 87-94, vol. 127(1).
Yellen et al. (1984) EMBO J. 3:2723-2730.
Waldron, et al. (1985) Plant Mol. Biol. 5:103-108.
Ward et al. (1993) Plant Mol. Biol. 22:361-366.
Zhang et al. (1991) Bio/Technology 9:996.
Zhijian et al. (1995) Plant Science 108:219-227.
Examination Report, mailed in related Australian Patent Application No. 2008218932, dated Oct. 9, 2012.

* cited by examiner

SEQUENCE LISTING

```
<160> NUMBER OF SEQ ID NOS: 6

<210> SEQ ID NO 1
<211> LENGTH: 3621
<212> TYPE: DNA
<213> ORGANISM: Sorghum Bicolor
<220> FEATURE:

<400> SEQUENCE: 1
ggtctaggca agagtttctt tgacataatg agtgggatgg aggctgcttt agcatctgga      60
gtgttgaagg ctgcaggtga caagctagtt tcactgttag ccactgagtt tgctgccata     120
accggtgtaa aaagagatct ctgccagctc caggatatac acgcagacat tacaggctgg     180
ctgtcggcag ggcatgatag agcaatacag agtgagacac agtctcactg ggtggtaaaa     240
ttgaaagatg tggcttatga cattgacgat atactacaag aagtccagct agaagctgag     300
aaacagaaga tggaaagaga tgatgacaag agtggtatag ctggttgctt ctgtgcaaaa     360
ccaaagtcat ttgcattccg atacaagatg gctcataaga tcaaggcaat caaggttaga     420
tttgctgcag ttgtcaagca aagaagtgat ttcaatactt tagttccaac aagggatcaa     480
catgttggta ctaggtacaa gacagttgga gagatgacct ggttgagcaa ggttccagag     540
tccaaaatac cccttaggga tcaagaaaag gatgaaatca tatctaagct tgtagaatgt     600
aatgctggag agaacaacat gatagtttct atcatcggat taggggggtc aggcaaaact     660
actttggcga aacacatttg ccatgacgtc aagataaagg agcactttgg aggtgaaata     720
ttctgggtcc atgtgtctca agagtttgat gttcagaagc tcatcggcaa gctatttgaa     780
acgattgttg gagataattc agatcgtcat cccccacagc acatggtcca aaaaatctcc     840
gagaagttga gcaataagaa gtttcttctt atccttgatg atgcttggca tgaggacaga     900
catgactggg aacagttcat ggtgcagcta aaatgtggcg cacctgaaac aaggattatg     960
ctaacgactc gtgatcgaaa ggttgcacaa gctgtggaat caagatatac atttgagttg    1020
gcattcttat cagagtctga gagttggaac ttattcctga agggttctgg gtttgcagag    1080
caagatttga gctccgatga ggtacaagtt ggaaaagata ttatcaaggg atgtggtggg    1140
gtgccgttag caattcaaac tcttggagca gtccttcgtg acaagaagca aataagtacg    1200
```

```
tggagggcca taagagagaa taatttatgg aaagttcaga gtataaaaga cagagtgttt    1260
gcatccttga agttgagcta tattcacttg gcagatgaac tgaagcagtg ctttacattt    1320
tgctccatat tcccgaaggg ctatggaatc cagaaagatc gtttgattgc caatggata    1380 gctcatggat tcatcaatgc aatgaatgga gagcaacccg aagatgttgg aagagactac    1440
ttagattctc ttgtaaatgt cagttttctt caggaagctt atgcgagctg aatactgat    1500 atatacaaca tgcatgattt gatccatgat ctcactcgac agatactaaa ggatgaactg    1560
gtgacttgtg ttccaattca tacaacagaa gaatttactc ataggtatag atatttatct    1620
ttgacttcat tcactgagaa tgttgacaag ggcgtatttg acaaggtccg tgctctatat    1680
atctctgaca gtaagccatc ttttgatacc acagtgaaga atagttgttg tatgcgcagt    1740
gttgttttgg actatgcaat tgatactccg ttttcactat tcatattaaa gtttgagtat    1800
cttgggtatc ttgaaattca taatgttagt tgtacaacag ttccagaagc tatctcgagg    1860
tgttggaact tgcagtcact ccattttgtt aactgcaaag gtttcgtgac attacctgag    1920
tctgttggaa agcttcagaa gctaaggact ctagagttgc ggcgcattat tgatattgag    1980
agtttgcctc agtccattgg tgactgttat gttcttcagt ccttgcaact atatgactgc    2040
agcatgctcc gagagatacc aagctcttta ggtagaattg gaagcctgtg tgtacttgat    2100
atagagcgtt gttcatctct gcaacaacta ccatcagaca tcattgggga gttcaaaaac    2160
ttgcgaacta tcaactttaa tggttgtacg ggtttgcaag acctgccaac cacattatcc    2220
tgtcctacat tgcgtactct gaacctttct ggaaccaaag ttaccatgct acctcaatgg    2280
gttacatcga ttggtactct agaatgtatt gaccttgagg gatgcaagga gctactggag    2340
ttgcctaagg gcatatcaaa cttgaaaagg ctcccagttt tgaacataaa gcattgtagt    2400
aaactctgct gcttaccaac agggttggga cagctgaccc gtttaagaga gctgggattg    2460
tttgttgttg ggtgtggtgc agatgatgcg aggatctcag agctagaaaa ccttgatatg    2520
ataggtggtc gcttggaaat taccaaccct aagtatttga aggatccaag tgatgcagag    2580
aaggcttgct tgaagcggaa gagtaacata caacacttgg agctgatctg gtctttaagt    2640
gatgccgaag aagagctggt gtcagatatg aacatgatt ggggtgtgct gaacgctctt    2700
gaaccaccat cgcaaattga gagcttggat atctatggtt acagaggccc ctgcctgcca    2760
ggatggatga tgaagcaaaa tgattctta tattgtgaag gtggcataat gctgaagcaa    2820
actgtcgcat cccatttcct ttgtttaact ttgttatcgc tagtaagatt tccaaacttg    2880
aggcatatga gaggatttgt tgagttgcct tcactgaaga cccttgagct ggcggaaatg    2940
cctaatttag aggagctgtg gactacatca agtggttttg aaactgggga aaagaattg    3000 gcagcacaac atcttttccc tgtcctgtcc agtctagaaa tatatggctg cccgaaatta    3060
aatgtgagcc cctactttcc accatcgttg gtgcatatgt cttaaacag aatcaatggg    3120 cagctgctat ccacaggaag gttctcccat cagctgccca gcatgcacgc gatggttctc    3180
cagagtctag tgctaagcga agttacagga tcatcatctg gctgggaact gctgcagcac    3240
ctcactgagc tgaaagagtt gtatattgac acgtgcaatg acctgacaca gttcccagag    3300
agcatgcgga acctcacctc gcttgaacat ctcgagctgt catcaggtcc tgcactgacg    3360
gtgctgccgg agtggattgg acaactctct gcgcttcgtt cgctttatat ccagcattcc    3420
cctgcccttc aatacttgcc ccaatccata caacgcctaa ctgctcttga ggaattgcgc    3480
atttatggtt gccctggttt ggcggagcgt tacaagcgag gggcagggcc cgactggcac    3540
cttgtcagtc acattcctct tgtggtaatc gatttcgtcg tgaatacggc aaatgcaacc    3600
```

```
gttggtaccg atgcattgta a                                          3621
```

<210> SEQ ID NO 2
<211> LENGTH: 561
<212> TYPE: DNA
<213> ORGANISM: Artificial Sequence
<220> FEATURE:
<223> OTHER INFORMATION: Synthetic polynucleotide

<400> SEQUENCE: 2

```
catgcctaat ttagaggagc tgtggactac atcaagtggt tttgaaactg gggagaaaga    60
attggcagca caatatcttt tccctgtcct gtccagtcta caaatatatg gctgcccaaa   120
attaaatgtg agcccctact ttccaccatc gttggagcgt atgactttag cagaaccaa    180
tgggcagttg ctatccgctg aaggttctc ccatcagctg cccagcatgc atgcgttggt    240
ccctcgcctc cagagtctag tgctaagcga agttacagga tcatcatctg gctgggaact   300
gctgcagcac tcactgagc tgaaagagtt gtgtatttac aggtgcaatg acctgacaca    360
gttaccagag agcatgcgga acctcacctc tctcgagcgt ctccgcatcg acgaatgccc   420
cgccgttggc acgttgcctg actggcttgg agaactgcac tctctgcgag accttgtatt   480
gggaatgggc gatttgaagc agttcccaga ggcgattcag cacctcacct cgcttgaaca   540
tctcgacctg ttatcaggcc c                                             561
```

<210> SEQ ID NO 3
<211> LENGTH: 414
<212> TYPE: DNA
<213> ORGANISM: Artificial Sequence
<220> FEATURE:
<223> OTHER INFORMATION: Synthetic polynucleotide

<400> SEQUENCE: 3

```
aatgcctaat ttagaggagc tgtggactac atcaagtggt tttgaaactg gggagaaaga    60
attggcagca caacatcttt tccctgtcct gtccagtcta gaaatatatg gctgcccgaa   120
attaaatgtg agcccctact ttccaccatc gttggtgcat atgtctttaa acagaatcaa   180
tgggcagctg ctatccacag aaggttctc ccatcagctg cccagcatgc acgcgatggt    240
tctccagagt ctagtgctaa gcgaagttac aggatcatca tctggctggg aactgctgca    300
gcacctcact gagctgaaag agttgtatat tgacacgtgc aatgacctga cacagttccc   360
agagagcatg cggaacctca cctcgcttga acatctcgag ctgtcatcag gtcc         414
```

<210> SEQ ID NO 4
<211> LENGTH: 561
<212> TYPE: DNA
<213> ORGANISM: Artificial Sequence
<220> FEATURE:
<223> OTHER INFORMATION: Synthetic polynucleotide

<400> SEQUENCE: 4

```
aatgcctaat ttagaggagc tgtggactac atcaagtggt tttgaaactg gggagaaaga    60
attggcagca caacatcttt tccctgtcct gtccagtcta gaaatatatg gctgcccaaa   120
attaaatgtg agcccctact ttccaccatc gttggagcat atgatttag tcagaaccaa    180
tgggcagttg ctatccactg aaggttctc ccatcagctg cccagcatgc atgcgttggt    240
ccctcgcctc aagagtctag tgctaagcga agttacagga tcatcatctg gctgggaact   300
gctgcagcac tcactgaac tgaaagagtt gtatttttac aggtgcaatg acctgacaca    360
gttaccagag agcatgcgga acctcacctc tctcgagcgt ctccgcatcg aggaatgccc   420
```

```
cgccgttggc acgttgcctg actggcttgg agaactgcat tctctgcgac accttggact    480
gggaatgggc gatttgaagc agttcccgga ggcgattcag cacctcacct cgcttgaaca    540
tctcgagctg tcatcaggtc g                                              561

<210> SEQ ID NO 5
<211> LENGTH: 23
<212> TYPE: DNA
<213> ORGANISM: Artificial Sequence
<220> FEATURE:
<223> OTHER INFORMATION: Synthetic primer

<400> SEQUENCE: 5
gaacatttct gccgccacat ttc                                             23

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
agcagttagg cgttgtatgg attg                                            24
```

COMPOSITIONS AND METHODS FOR IDENTIFYING GENETIC SEQUENCES WITH TOXIN RESISTANCE IN PLANTS

STATEMENT REGARDING RELATED APPLICATIONS

This application claims priority to U.S. Provisional Patent Application 60/891,302, filed Feb. 23, 2007, and U.S. Provisional Patent Application 60/986,097, filed Nov. 7, 2007.

STATEMENT REGARDING FEDERALLY FUNDED RESEARCH

Two U.S. Department of Agriculture grants, number 2006/63531917462 and number 033043-1, were used to fund research associated with this application; the federal government may have certain rights in it.

FIELD OF THE INVENTION

This invention relates generally to useful compositions and methods related to plant site-directed recombination. In particular, the invention relates to novel nucleic acid sequences unique to a portion of the *sorghum* NBS-LRR region, as well as vectors, seeds, plant parts and plants comprising these sequences. Methods to investigate recombination co-factors, and methods to investigate potential herbicides are within the scope. This invention also relates to fungal pathogens of *sorghum*, particularly *Periconia circinata*.

BACKGROUND OF THE INVENTION

Plant pathogen damage, whether in the crop field or flower garden, has been an expensive and nearly insurmountable problem since agriculture first began. Co-evolution of plant and pathogen defines two solutions: outwitting the pathogen or helping the plant. Our modern approach has been to do both, while simultaneously assuring that associated ecosystems are not permanently damaged.

Various approaches address the ongoing power struggle between plant and plant pathogen. Since many important pathogens fall into the category of "biotrophic" or healthy tissue-needing pathogens, most research is directed at understanding them. Another class of pathogens, the "necrotrophs," flourish when plants are weakened. The present invention arises out of study of a necrotrophic relationship between pathogen and plant.

Even though plants do not have immune systems in the mammalian sense of specialized secretory cells, they do possess the ability to avoid or minimize pathogen-induced damage and/or disease. Prior to the present invention, it was thought that the most frequent route for a species to avoid "extinction by pathogens" was one of two ways: programmed cell death at a pathogen's invasion site, and random mutation during meiosis to alter the specificity of pathogen recognition.

Programmed cell death (or "apoptosis") at the site of invasion is a well-characterized phenomenon in plants, with particular gene groups, especially the "NBS-LRR" (nucleotide binding site, leucine-rich repeat), being known as a rich source of resistance genes. In plant genomes that have been studied for the presence of NBS-LRR regions (approximately 45), all have been found to contain them. The present invention provides a previously-uncharacterized resistance gene from *sorghum*.

The second type of extinction avoidance, crossover events and point mutations during meiosis, results in plants that have new disease resistance gene specificities. Any new trait makes it possible that any given environment can select that trait as preferred. Much research goes into accelerating this normal process via plant breeding programs and molecular biology. Designing and/or selecting preferred traits in plants is a worldwide, billion dollar industry, with consumer and/or legislative pressures favoring plant breeding over programs that result in "GMO" programs. The present invention provides wholesome methods to speed traditional plant breeding processes.

On the other side of the equation, pathogen physiology and genetics research are sources of knowledge that can lead to new herbicides, insecticides and fungicides. In a twist on the common approach, some agriculturists study the use of pathogens (primarily insects and fungi) to kill weeds. Fungal isolates have been disclosed in the past which selectively kill invasive species.

Target specificity to specific plant species is a desired attribute of any herbicide; however, herbicides that are overly specific have markets that are too small to justify investment. Tools that decrease the cost of bringing a very specific herbicide to market would benefit investors as well as the environment. The present invention provides methods to identify such environmentally-friendly and economically-feasible herbicides.

As an example to the tenets previously described, *Sorghum bicolor* is a dietary staple of more than 500 million people worldwide. In the United States, *sorghum* provides an economical alternative to corn for use as ethanol biomass. Moreover, *sorghum* does not produce gluten, making it particularly useful as an alternative to wheat in the making of food and a beverages for gluten-intolerant individuals.

*Sorghum*, like other grain crops, is a target for a variety of pathogens. Some *sorghum* pathogens enter the plant un-recognized, and impair the plant. Some individual *sorghum* plants, however, recognize biotrophic pathogens (via distinctive surface or secreted chemicals), and mount a successful hypersensitive response, causing the site of infection to wither and die. The localized cell death starves the biotrophic, prevents further damage, and saves the plant. In this way, successful individual plants live to breed and pass their life-saving trait to future generations. However, the same is true of individual pathogens; some avoid being recognized by these newly-sensitive plants. This recognition/non-recognition process is an "arms race" between pathogen and plant. Dramatic shifts in plant and pathogen populations appear within as little as ten years.

Milo disease of *sorghum* is an example of a plant disease caused by a necrotroph. A plant with *Periconia* infection has dark red discoloration on the roots and crown. The leaves become chlorotic and eventually die. The infected plants produce little or no grain.

However, some individual *sorghum* plants do not respond to *Periconia*. These non-reactive plants grow normally, even if exposed to the *Periconia* fungus. In other words, these non-reactive *sorghum* plants are resistant to milo disease by not responding to *Periconia*'s chemical cues.

Susceptibility to *Periconia* peritoxin and milo disease is provided by a single, semi-dominant gene, Pc. Pc naturally mutates to the resistant pc allele at a rate of about one per 8000 gametes. This high level of instability is unidirectional: pc to Pc mutations have not been observed.

Understanding the phenomena of milo disease susceptibility and resistance in *sorghum* adds value to agricultural research, development and commercialization in a wide variety of plants, and for the benefit of a wide variety of consumers.

Moreover, the evolutionary battle of pathogen vs. plant will unfold indefinitely because plants and pathogens each have their own mechanisms for avoiding extinction. Therefore, any new means for: 1. accelerating new plant development; 2. accelerating new herbicide development; and/or 3. accelerating our common wisdom in any of these fields, is useful and needed. The present invention provides tools and methods related to all three of these goals.

SUMMARY OF THE INVENTION

The present invention provides isolated polynucleotides comprising at least 20 contiguous bases of bases 3062-3622 of an LRR region of *Sorghum bicolor*. Preferred are those polynucleotides which are at least 40 contiguous bases. Also preferred are those which are selected from the group consisting of the following contiguous bases: 30, 35, 45, 50, 55, 60, 65, 70, 75, 80, 85, 90, 95, 100, and any other increment of 5, continuing to 560 bases. In particular, those polynucleotides selected from the group consisting of: SEQ ID NO:2; SEQ ID NO:3; SEQ ID NO:4; SEQ ID NO:5; and SEQ ID NO:6 are most preferred.

Also provided are vectors comprising at least two polynucleotides having at least 20 contiguous bases, although previously-mentioned numbers of contiguous bases are also provided. Vectors which comprise the polynucleotides described and which further comprise an expression control polynucleotide and a polynucleotide of interest are also provided. Preferred are those vectors now described, which further comprises a marker polynucleotide.

Also provided are cultured cells comprising vectors described herein. Seeds, plants, plant parts, roots, calluses and leaves comprising at least two polynucleotides of the present invention are preferred, although those plant parts which comprise one polynucleotide, or multiple polynucleotides are also provided.

Also provided are isolated polynucleotides comprising at least 70% identity to bases 3062-3622 of an LRR region of *Sorghum bicolor*. Preferred are those polynucleotides comprising at least 90% identity, although those polynucleotides that comprise 75, 80, 85, 95, 96, 97, and 98 percent identity are also provided.

Also provided are vectors comprising at least two polynucleotides described above, although those vectors comprising one or multiple polynucleotides described above are also provided. Those vectors which further comprise an expression control polynucleotide and a polynucleotide of interest are preferred. Most preferred are those vectors, as described, which further comprise a marker polynucleotide.

Cultured cells comprising vectors described herein are provided, as are cell cultures comprising a blend of cells, and/or a library of polynucleotides in vectors herein described.

Seeds, plants, plant parts, roots, calluses and leaves comprising at least two polynucleotides of the present invention are preferred, although those plant parts which comprise one polynucleotide, or multiple polynucleotides are also provided.

Also provided are methods to identify a polynucleotide that contributes to recombination, comprising: culturing a cell described herein, under conditions suitable for expression of said polynucleotide of interest, and determining if recombination occurs. Any acceptable methods are included, specifically, preferred methods are those wherein said identification is selected from the group consisting of: marker identification; phenotypic changes; genotypic changes.

Also provided are isolated polynucleotides comprising at least 70% identity with the polynucleotide of SEQ ID NO: 1. Those wherein said polynucleotide is at least 90% identical to said SEQ ID NO:1 are preferred; however, those polynucleotides that comprise 75, 80, 85, 95, 96, 97, and 98 percent identity are also provided.

Vector comprising these polynucleotides are provided, particularly preferred are expression vectors comprising an expression control polynucleotide operably linked to a polynucleotide herein described.

Moreover, cultured cells comprising vectors described herein are provided, as are cell cultures comprising a blend of cells, and/or a library of polynucleotides in vectors herein described.

Seeds, plants, plant parts, roots, calluses and leaves comprising at least two polynucleotides of the present invention are preferred, although those plant parts which comprise one polynucleotide, or multiple polynucleotides are also provided.

Also provided are methods to identify if a test compound interacts with an expression product of at least one polynucleotide of the present invention, comprising contacting a test compound with an expression product of a Pc gene sequence, and determining whether the test compound interacts with said expression product.

These and other features and advantages of this invention will become more apparent to those skilled in the art from the detailed description.

DEFINITIONS

"Marker polynucleotide" has the same meaning as "marker," as that term is used in the art.

"Expression control polynucleotide" means any polynucleotide which affects expression.

"Interacts" means causing any chemical change, phenotypic change, or genotypic change, including, for example only: binding or regulating.

"Vector" means any nucleic acid construct which is able to enter a plant cell, including circular or linear nucleic acids, and/or bacterial, viral, fungal, plant and synthesized nucleic acids, as well as homologous or heterologous nucleic acid constructs.

DETAILED DESCRIPTION

Figure 1:
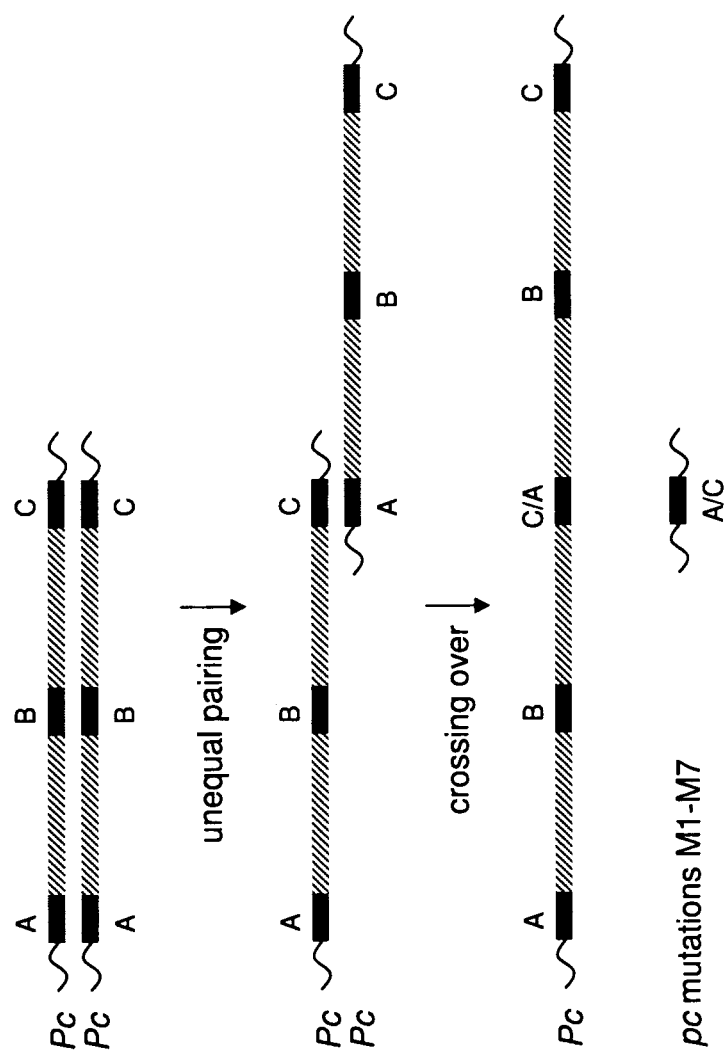
FIG. 1. Unequal recombination events between paralogues A and C in Pc-mutants M1-M7.
Figure 2:
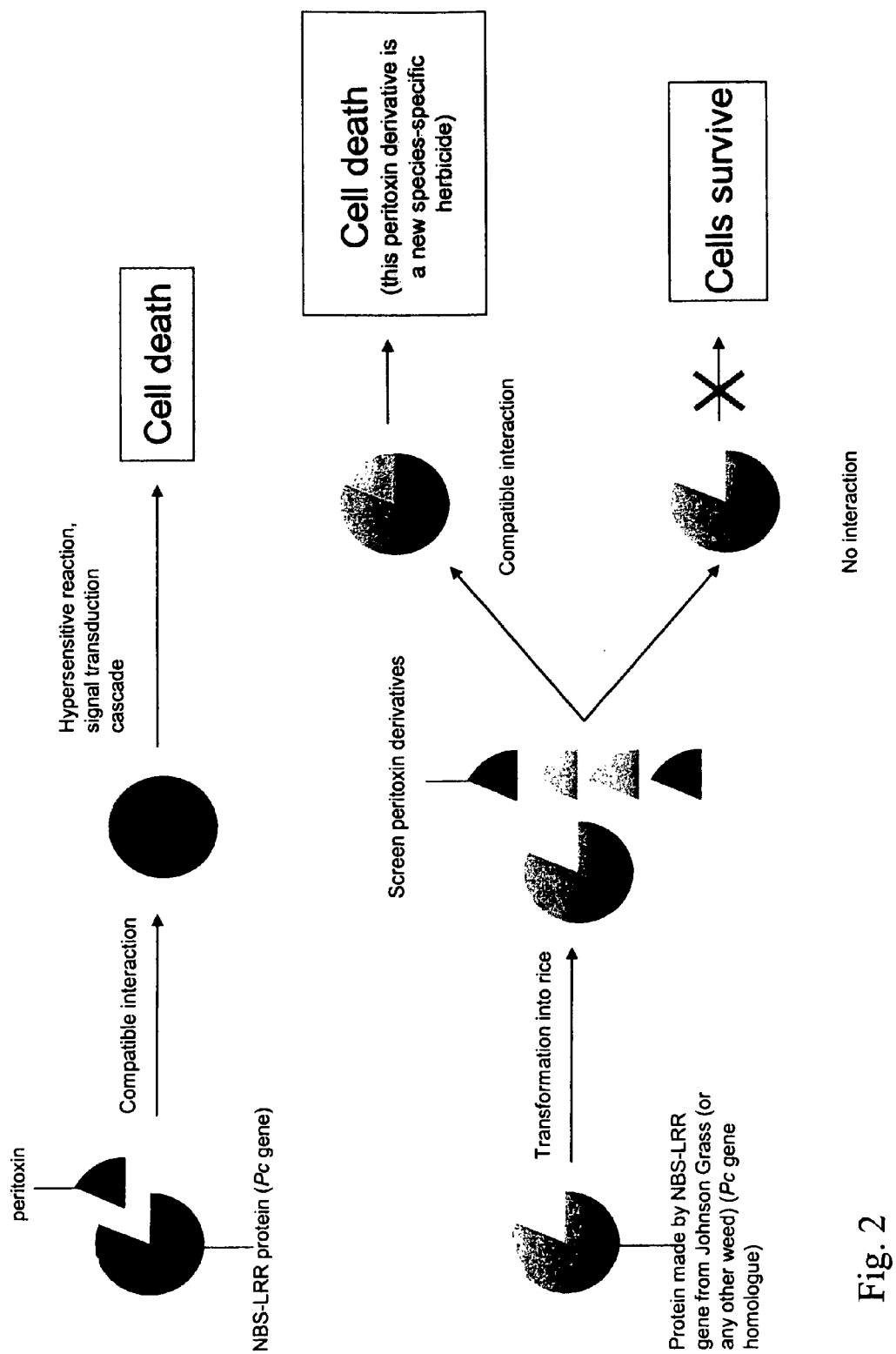
FIG. 2. Schematic of exemplified methods of the present invention.
Figure 3:
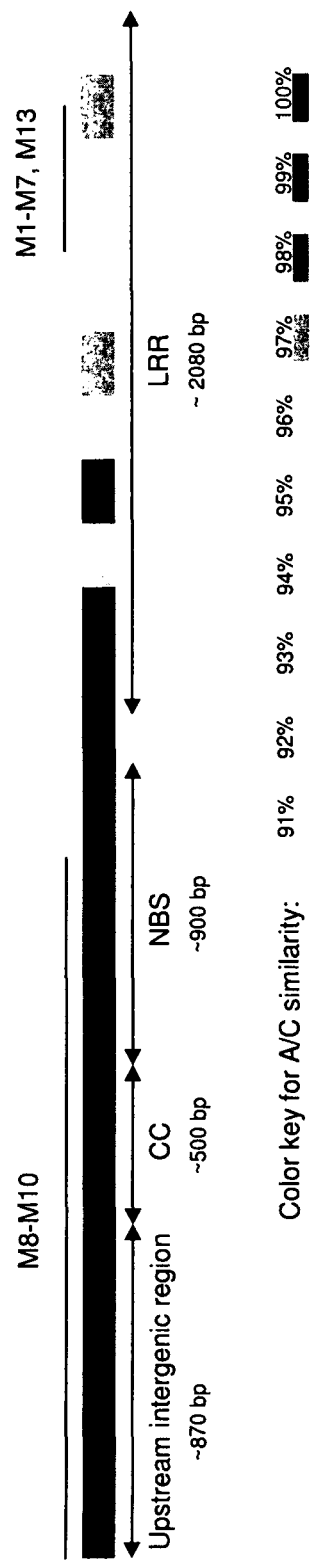
FIG. 3. Localization of the unequal recombination breakpoints between paralogues A and C along their consensus sequence (3737 bp). The degree of similarity between paralogues A and C is shown with a color code. Three unequal recombinations (in mutants M8-M10) occurred either in upstream intergenic regions or in the 5' regions that are identical between paralogues A and C. Nine of the A-C recombinations (one each in M1-M7, two in M13) were localized in a less conserved, 560 bp segment of the LRR region (for more details see Table 1).
Figure 4:
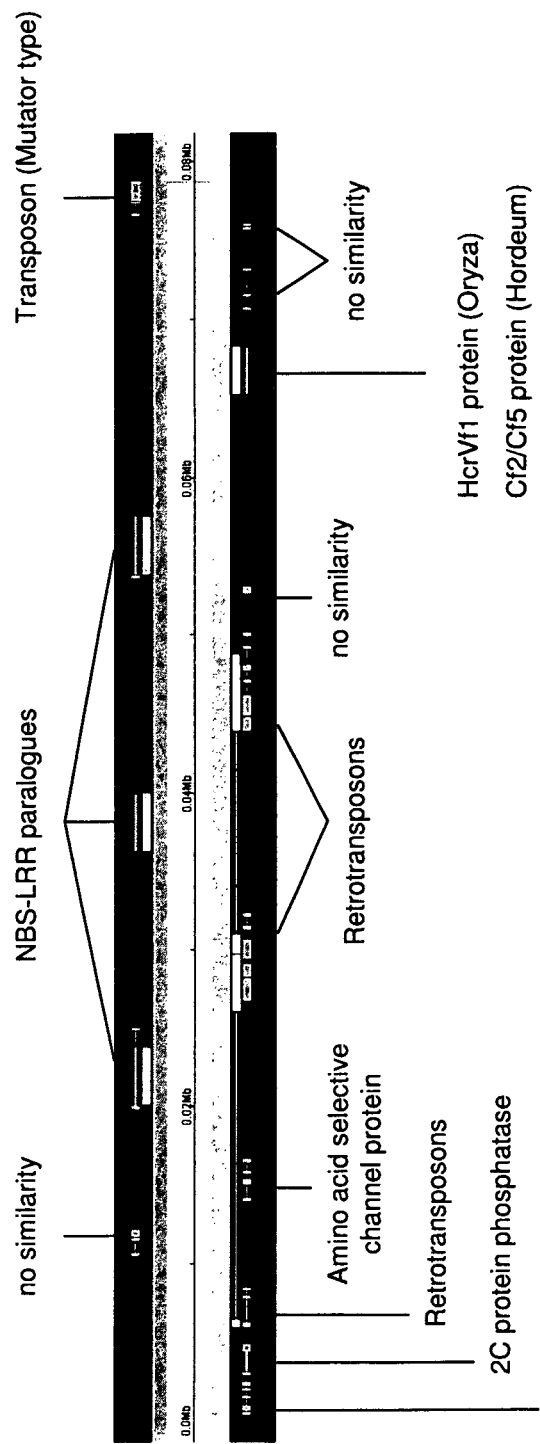
FIG. 4. Gene annotation of the Pc-region in the *sorghum* cultivar Colby as demonstrated by the software, Apollo. The two horizontal blue stripes represent the two complementary DNA strands. The annotation results are shown in the black fields. The yellow blocks represent the gene-homologies found with the program BLASTX, the purple blocks are for the gene prediction results (FGENESH). The NBS-LRR gene family on the plus strand included the Pc gene.

The elucidation of the present materials and mechanism of action of the materials in situ offers other, similar materials, as well as plant breeding methods and new herbicide investigation methods.

In the broadest sense, the present invention provides plant genetic materials and methods. The materials fall into a variety of categories, including: polynucleotides; polypeptides; vectors; seeds; plants; and plant parts. The methods can be described generically as: methods to construct and utilize vectors; methods to identify and express genes; methods to transfect and/or transform seeds, plants and/or plant parts; methods to cause polypeptides to recombine; methods to cause site-specific recombination of polypeptides; methods to assay compounds and methods to locate recombination co-factors.

The term plant includes plant cells, plant protoplasts, plant cell tissue cultures from which plants can be regenerated, plant calli, plant clumps, and plant cells that are intact in plants or parts of plants such as embryos, pollen, ovules, seeds, flowers, kernels, ears, cobs, husks, stalks, roots, root tips, anthers, and the like.

The specification and claims use the singular forms "a," "an," and "the." These terms are intended to not exclude a plural interpretation, and may preferably include a plural interpretation, depending on the context. Thus, for example, reference to "a compound" may include a variety of such compounds, or several of those same compounds, unless the interpretation is contrary to the context in which it is used.

With regard to the polynucleotides herein disclosed, the preferred polynucleotides are exemplified by Paralogues A, B, and C of the *sorghum* NBS-LRR region.

The term polynucleotide encompasses the terms "nucleic acid," "nucleic acid sequence," or "oligonucleotide" as those terms are generally understood in the art.

Further, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

Numerous methods for introducing foreign genes into plants are known and can be used to insert nucleic acid sequences into a plant host, including biological and physical plant transformation protocols. See, for example, Miki et al. (1993) "Procedure for Introducing Foreign DNA into Plants," in *Methods in Plant Molecular Biology and Biotechnology*, ed. Glick and Thompson (CRC Press, Inc., Boca Raton), pages 67-88. The methods chosen vary with the host plant, and include chemical transfection methods such as calcium phosphate, microorganism-mediated gene transfer such as *Agrobacterium* (Horsch et al. (1985) *Science* 227:1229-1231), electroporation, micro-injection, and biolistic bombardment.

Expression cassettes and vectors and in vitro culture methods for plant cell or tissue transformation and regeneration of plants are known and available. See, for example, Gruber et al. (1993) "Vectors for Plant Transformation," in *Methods in Plant Molecular Biology and Biotechnology*, ed. Glick and Thompson (CRC Press, Inc., Boca Raton), pages 89-119.

The most widely utilized method for introducing an expression vector into plants is based on the natural transformation system of *Agrobacterium*. *A. tumefaciens* and *A. rhizogenes* are plant pathogenic soil bacteria that genetically transform plant cells. The Ti and Ri plasmids of *A. tumefaciens* and *A. rhizogenes*, respectfully, carry genes responsible for genetic transformation of plants. See, for example, Kado (1991) *Crit. Rev. Plant Sci.* 10:1. Descriptions of the *Agrobacterium* vector systems and methods for *Agrobacterium*-mediated gene transfer are provide in Gruber et al. (1993), supra; Miki et al. (1993), supra; and Moloney et al. (1989) *Plant Cell Reports* 8:238.

Despite the fact that the host range for *Agrobacterium*-mediated transformation is broad, some major cereal crop species and gymnosperms have generally been recalcitrant to this mode of gene transfer, even though some success has recently been achieved in rice (Hiei et al. (1994) *Plant J.* 6:271-282) and maize (Ishida et al. (1996) *Nature/Biotechnology* 14:745-750). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 µm. The DNA generally contained in an expression vector expression vector is introduced into plant tissues with a biolistic device that accelerates the microprojectiles to speeds of 300 to 600 m/s, which is sufficient to penetrate the plant cell walls and membranes (Sanford et al. (1987) *Part. Sci. Technol.* 5:27; Sanford (1988) *Trends Biotech.* 6:299; Sanford (1990) *Physiol. Plant.* 79:206; Klein et al. (1992) *Biotechnology* 10:268).

Another method for physical delivery of DNA to plants is sonication of target cells as described in Zang et al. (1991) *Bio/Technology* 9:996. Alternatively, liposome or spheroplast fusions have been used to introduce expression vectors into plants. See, for example, Deshayes et al. (1985) *EMBO J.* 4:2731; and Christou et al. (1987) *Proc. Natl. Acad. Sci. USA* 84:3962. Direct uptake of DNA into protoplasts using CaCl2 precipitation, polyvinyl alcohol, or poly-L-ornithine have also been reported. See, for example, Hain et al. (1985) *Mol. Gen. Genet.* 199:161; and Draper et al. (1982) *Plant Cell Physiol.* 23:451.

Electroporation of protoplasts and whole cells and tissues has also been described. See, for example, Donn et al. (1990) in *Abstracts of the VIIth Int'l. Congress on Plant Cell and Tissue Culture (IAPTC)* A2-38, page 53; D'Halluin et al. (1992) *Plant Cell* 4:1495-1505; and Spencer et al. (1994) *Plant Mol. Biol.* 24:51-61. Microinjection of DNA into whole plant cells has also been described as has microinjection into protoplasts. See, for example in whole cells, Neuhaus et al. (1987) *Theor. Appl. Genet.* 75:30-36; and in protoplasts, Crossway et al. (1986) *Mol. Gen. Genet.* 202:179-185; and Reich et al. (1986) *Biotechnology* 4:1001-1004.

Another useful basic transformation protocol involves a combination of wounding by particle bombardment, followed by use of *Agrobacterium* for DNA delivery, as described by Bidney et al. (1992) *Plant Mol. Biol.* 18:301-313. Useful plasmids for plant transformation include PHP9762. The binary backbone for PHP9762 is bin 19. See Bevan et al. (1984) *Nucleic Acids Res.* 12:8711-8721.

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterium*. To start the co-cultivation for intact meristems, *Agrobacterium* is placed on the meristem. After about a 3-day co-cultivation period the meristems are transferred to culture medium with cefotaxime (plus kanamycin for the NPTII selection). Selection can also be done using kanamycin.

The split meristem method involves imbibing seed, breaking of the cotyledons to produce a clean fracture at the plane of the embryonic axis, excising the root tip, and then bisecting the explants longitudinally between the primordial leaves. The two halves are placed cut surface up on the medium then bombarded twice with particles, followed by co-cultivation with *Agrobacterium*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime (plus kanamycin for selection).

Once a single transformed plant has been obtained by the foregoing recombinant DNA method, e.g., a plant transformed with a desired gene, conventional plant breeding methods can be used to transfer the structural gene and associated regulatory sequences via crossing and backcrossing. In general, such plant breeding techniques are used to transfer a desired gene into a specific crop plant. In the instant invention, such methods include the further steps of: (1) sexually crossing a transformed plant comprising the present sequences with a second co-factor transformed plant; (2) recovering reproductive material from the progeny of the cross; and (3) growing dually transformed plants from the reproductive material.

The present polynucleotides may be used to advantageously excise a gene from a plant genome. For example, a marker gene may be inserted into a plant genome along with a gene of interest. The marker gene is initially useful in demonstrating effective transformation of the plants, but is not desired in the final product. By inducing expression, transiently or from the plant's genome, the unwanted marker gene is excised.

In other examples, a target site is constructed to have multiple functional sets of dissimilar and non-recombinogenic recombination sites. Thus, multiple genes or polynucleotides can be stacked or ordered. In specific examples, this method allows for the stacking of sequences of interest at precise locations in the genome of a cell or an organism. Likewise, once a target site has been established within a cell or an organism, additional recombination sites may be introduced by incorporating such sites within the transfer cassette. Thus, once a target site has been established, it is possible to subsequently add sites or alter sites through recombination. Such methods are described in detail in WO 99/25821.

In one example, methods to combine multiple transfer cassettes are provided. The method comprises providing a target site comprising at least a first and a second functional recombination site, wherein the first and the second recombination sites are dissimilar and non-recombinogenic with respect to one another. A first transfer cassette comprising in the following order at least the first, a third, and the second functional recombination sites is provided wherein the first and the third recombination sites of the first transfer cassette flank a first polynucleotide of interest and wherein the first, the second, and the third recombination sites are dissimilar and non-recombinogenic with respect to one another and a first recombinase is provided, whereby the first transfer cassette is integrated at the target site. At least one of the first, the second, or the third recombination sites comprise a functional modified recombination site provided herein.

Methods of alignment of sequences for comparison are well known in the art. Optimal alignment of sequences for comparison may be conducted by the local homology algorithm of Smith and Waterman (1981) *Adv. Appl. Math.* 2:482; by the homology alignment algorithm of Needleman and Wunsch (1970) *J. Mol. Biol.* 48:443; by the search for similarity method of Pearson and Lipman (1988) *Proc. Natl. Acad. Sci. USA* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis.; the CLUSTAL program is well described by Higgins et al. (1988) *Gene* 73:237-244; Higgins et al. (1989) *CABIOS* 5:151-153; Corpet et al. (1988) *Nucleic Acids Res.* 16:10881-90; Huang et al. (1992) *Computer Applications in the Biosciences* 8:155-65, and Person et al. (1994) *Meth. Mol. Bio.* 24:307-331; preferred computer alignment methods also include the BLASTP, BLASTN, and BLASTX algorithms. See Altschul et al. (1990) *J. Mol. Biol.* 215:403-410. Alignment is also often performed by inspection and manual alignment.

"Sequence identity" or "identity" in the context of two nucleic acid or polypeptide sequences includes reference to the residues in the two sequences that are the same when aligned for maximum correspondence over a specified comparison window. When percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

Those in the art recognize that the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Moreover, one of skill in the art will recognize that the sequence identity values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%. Polypeptides that are "substantially similar" share sequences as noted above except that residue positions, which are not identical, may differ by conservative amino acid changes.

Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60° C. However, nucleic acids which do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide encoded by the first nucleic acid is immunologically cross reactive with the polypeptide encoded by the second nucleic acid.

For a description of various libraries, vectors, nucleic acids, etc., see, for example, Stratagene Cloning Systems, Catalogs 1999 (La Jolla, Calif.); and, Amersham Life Sciences, Inc, Catalog '99 (Arlington Heights, Ill.).

The isolated proteins of the present invention comprise a polypeptide having at least 10 amino acids from a polypeptide of the present invention (or conservative variants thereof) such as those encoded by any one of the polynucleotides of the present invention. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

The present invention further provides a protein comprising a polypeptide having a specified sequence identity/similarity with a polypeptide of the present invention. The percentage of sequence identity/similarity is an integer selected from the group consisting of from 50 to 99. Exemplary sequence identity/similarity values include 55%, 60%, 65%, 70%, 75%, 80%, 85%, 90%, and 95%. Sequence identity can be determined using, for example, the GAP, CLUSTALW, or BLAST algorithms, preferably BLAST.

As those of skill will appreciate, the present invention includes, but is not limited to, catalytically active polypeptides of the present invention (eg., SEQ ID NO:1). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay. Thus, the proteins of the present invention can be employed as immunogens for constructing antibodies immunoreactive to a protein of the present invention for such exemplary utilities as immunoassays or protein purification techniques.

Using the nucleic acids of the present invention, one may express a protein of the present invention in a recombinantly engineered cell such as bacteria, yeast, insect, mammalian, or preferably plant cells.

It is expected that those of skill in the art are knowledgeable in the numerous expression systems available for expression of a nucleic acid encoding a protein of the present invention. Those in the art recognize that certain variations do not result in undue experimentation, and those variations are included in the scope of the present invention.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Labo-* ratory Manual (2d ed., Cold Spring Harbor Laboratory Press, Plainview, N.Y.). and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

Preferred are those sequences isolated and used in the present methods, from the following plants:

Examples of plant genuses and species of interest to locate co-factors of the present recombinatory sequences include, but are not limited to, monocots and dicots such as corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena*), barley (*Hordeum*), palm, legumes including beans and peas such as guar, locust bean, fenugreek, garden beans, cowpea, mungbean, lima bean, fava bean, lentils, chickpea, and castor, *Arabidopsis*, vegetables, ornamentals, grasses, conifers, crop and grain plants that provide seeds of interest, oil-seed plants, and other leguminous plants. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include, for example, pines such as loblolly pine (*Pinus taeda*), slash pine (*Pinus elliotil*), ponderosa pine (*Pinus ponderosa*), lodgepole pine (*Pinus contorta*), and Monterey pine (*Pinus radiata*); Douglas-fir (*Pseudotsuga menziesil*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The isolated nucleic acids of the present invention can also be prepared by direct chemical synthesis by methods such as the phosphotriester method of Narang et al., Meth. Enzymol. 68:90-99 (1979); the phosphodiester method of Brown et al., Meth. Enzymol. 68:109-151 (1979); the diethylphosphoramidite method of Beaucage et al., Tetra. Lett. 22:1859-1862 (1981); the solid phase phosphoramidite triester method described by Beaucage and Caruthers, Tetra. Letts. 22(20): 1859-1862 (1981), e.g., using an automated synthesizer, e.g., as described in Needham-VanDevanter et al., Nucleic Acids Res. 12:6159-6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

The nucleic acids of the present invention include those amplified using the following primer pairs: SEQ ID NOS: 5 and 6.

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook et al.; *Molecular Cloning: A Laboratory Manual*; Cold Spring Harbor, N.Y. (1989); Gelvin et al.; *Plant Molecular Biology Manual* (1990); *Plant Biotechnology: Commercial Prospects and Problems*, eds. Prakash et al.; Oxford & IBH Publishing Co.; New Delhi, India; (1993); and Heslot et al.; *Molecular Biology and Genetic Engineering of Yeasts*; CRC Press, Inc., USA; (1992.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the actin promoter, the ubiquitin promoter, the histone H2B promoter (Nakayama et al., 1992, FEBS Lett 30:167-170), the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known in the art.

Examples of inducible promoters are the Adh1 promoter which is inducible by hypoxia or cold stress, the Hsp70 promoter which is inducible by heat stress, the PPDK promoter which is inducible by light, the In2 promoter which is safener induced, the ERE promoter which is estrogen induced and the Pepcarboxylase promoter which is light induced.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; Plant Sci. 47:95-102 (1986) and Reina, M., Ponte, I., Guillen, P., Boronat, A. and Palau, J., Sequence analysis of a genomic clone encoding a Zc2 protein from *Zea mays* W64 A, Nucleic Acids Res. 18(21):6426 (1990). See the following site relating to the waxy promoter: Kloesgen, R. B., Gierl, A., Schwarz-Sommer, Z. S. and Saedler, H., Molecular analysis of the waxy locus of *Zea mays*, Mol. Gen. Genet. 203:237-244 (1986). The disclosures each of these are incorporated herein by reference in their entirety.

Vectors may be constructed using standard molecular biology techniques. See, for example, Sambrook et al. (1989) *Molecular Cloning: A Laboratory Manual* (2d ed., Cold Spring Harbor Laboratory Press, Plainview, N.Y.). Plasmids are based on pUC18. The vectors preferred contain combinations of the same basic regulatory elements. The Omega prime (O—) 5-prime sequence is described by Gallie et al. (1987) *Nucleic Acids Res.* 15:3257-3273. The selective marker gene bar (Thompson et al. (1987) *EMBO J.* 6:2519-2523) may be used in conjunction with bialaphos selection to recover transformants. The Cauliflower Mosaic Virus 35S promoter with a duplicated enhancer region is described by Gardner et al. (1981) *Nucleic Acid Res.* 9:2871-2888. The 79-bp Tobacco Mosaic Virus leader is described by Gallie et al. (1987) *Nucleic Acid Res.* 15:3257-3273 and may be inserted downstream of the promoter followed by the first intron of the maize alcohol dehydrogenase gene ADH1-S, described by Dennis et al. (1984) *Nucleic Acid Res.* 12:3983-3990. The 3-prime sequence pinII is described by An et al. (1989) *Plant Cell* 1:115-122.

A variety of inducible promoters can be used in the instant invention. See, Ward et al. (1993) *Plant Mol. Biol.* 22:361-366. Exemplary inducible promoters include that from the ACE1 system, which responds to copper (Mett et al. (1993) *Proc. Natl. Acad. Sci. USA* 90:4567-4571); In2 gene from maize, which responds to benzenesulfonamide herbicide safeners (Hershey et al. (1991) *Mol. Gen. Genet.* 227:229-237 and Gatz et al. (1994) *Mol. Gen. Genet.* 243:32-38), or Tet repressor from Tn10 (Gatz et al. (1991) *Mol. Gen. Genet.* 227:229-237. A particularly preferred inducible promoter is a promoter that responds to an inducing agent to which plants do not normally respond. An exemplary inducible promoter is the inducible promoter from a steroid hormone gene the transcriptional activity of which is induced by a glucocorticosteroid hormone. See Schena et al. (1991) *Proc. Natl. Acad. Sci. USA* 88:10421.

The expression vector comprises an inducible promoter operably linked to a nucleotide sequence encoding the sequences herein. The expression vector is introduced into plant cells and presumptively transformed cells are exposed to an inducer of the inducible promoter. The cells are screened for the presence of the sequences proteins by introducing a sequences herein that upon excision, promotes expression of a scorable marker such as GUS, GFP, luciferase, or anthocyanin production.

A number of tissue-specific or tissue-preferred promoters can be utilized in the instant invention. Exemplary tissue-specific or tissue-preferred promoters include a root-preferred promoter such as that from the phaseolin gene (Murai et al. (1983) *Science* 23:476-482 and Sengupta-Gopalan et al. (1985) *Proc. Natl. Acad. Sci. USA* 82:3320-3324); a leaf-specific and light-induced promoter such as that from cab or rubisco (Simpson et al. (1985) *EMBO J.* 4(11):2723-2729 and Timko et al. (1985) *Nature* 318:579-582); an anther-specific promoter such as that from LAT52 (Twell et al. (1989) *Mol. Gen. Genet.* 217:240-245); a pollen-specific promoter such as that from Zm13 (Guerrero et al. (1993) *Mol. Gen. Genet.* 224:161-168) or a microspore-preferred promoter such as that from apg (Twell et al. (1993) *Sex. Plant Reprod.* 6:217-224).

Many different constitutive promoters can be utilized in the instant invention. Exemplary constitutive promoters include the promoters from plant viruses such as the 35S promoter from CaMV (Odell et al. (1985) *Nature* 313:810-812) and the promoters from such genes as rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); and maize H3 histone (Lepetit et al. (1992) *Mol. Gen. Genet.* 231: 276-285 and Atanassova et al. (1992) *Plant J.* 2(3):291-300).

The ALS promoter, a XbaI/NcoI fragment 5-prime to the *Brassica napus* ALS3 structural gene (or a nucleotide sequence that has substantial sequence similarity to said XbaI/NcoI fragment), represents a particularly useful constitutive promoter. See co-pending Pioneer Hi-Bred International U.S. application Ser. No. 08/409,297.

In one embodiment of the present invention, expression co-factors of the presently-described polynucleotides can be used to modify transgenic sequences that have been previously integrated into the maize genome. In such a manner, structural genes whose DNA sequence and/or gene-expression are not desired in the final product can be removed. Thus, marker genes that have utility in the recovery of transgenic events in culture (or during plant growth or reproduction) can be removed from a transgenic event, leaving intact, expressing agronomic expression cassettes in the final product. In the process of excising one sequence, a structural gene can also be moved relative to a promoter to activate the gene (i.e., simply by moving the structural gene next to the promoter, through the removal of transcriptional impediments such as polyA sequences or stop-codons, or through frame shifts).

Depending on the transformation strategy and the desired final product, many of the genes listed below could be candidates for marker genes used for recovery of transgenics during transformation that would later be removed from the final commercial product, and also for agronomically important genes to be expressed in the final product (for example, herbicide genes).

In addition, a marker gene for identifying and selecting transformed cells, tissues, or plants should be included in the transformation construct. By marker gene is intended to be either reporter genes or selectable marker genes.

Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; Chiu et al. (1996) *Current Biology* 6:325-330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Bio.* 15:127-136); bromoxynil (Stalker et al. (1988) *Science* 242:419-423); glyphosate (Shaw et al. (1986) *Science* 233:478-481); phosphinothricin (DeBlock et al. (1987) *EMBO J.* 6:2513-2518).

Other genes that could serve utility in the recovery of transgenic events but might not be required in the final product would include, but are not limited to, such examples as GUS (β-glucoronidase; Jefferson (1987) *Plant Mol. Biol. Rep.* 5:387), GFP (green fluorescence protein; Chalfie et al. (1994) *Science* 263:802), and the maize genes encoding for anthocyanin production (Ludwig et al. (1990) *Science* 247: 449). For certain applications, for example the commercial production of harvestable protein from transgenic plants as described below, expression of the above genes would be valuable and thus would remain after excision.

Numerous types of genes fall into the category of potentially valuable genes that would remain in the final commercial transgenic event after excision of various unwanted (or simply unnecessary) transgenic elements. Examples are included below.

With transgenic plants according to the present invention, a foreign protein can be produced in commercial quantities. Thus, the selection and propagation techniques described above yield a plurality of transgenic plants that are harvested in a conventional manner, and a foreign protein then is extracted from a tissue of interest or from total biomass. Protein extraction from plant biomass can be accomplished by known methods, which are discussed, for example, by Heney et al. (1981) *Anal. Biochem.* 114: 92-6.

Likewise, by means of the present invention, agronomic genes can be expressed in transformed plants. More particularly, plants can be genetically engineered to express various phenotypes of agronomic interest. The genes implicated in this regard include, but are not limited to, those categorized below.

Plant disease resistance genes. Plant defenses are often activated by specific interaction between the product of a disease resistance gene (R) in the plant and the product of a corresponding avirulence (Avr) gene in the pathogen. A plant variety can be transformed with a cloned resistance gene to engineer plants that are resistant to specific pathogen strains. See, for example, Jones et al. (1994) *Science* 266:789 (cloning of the tomato Cf-9 gene for resistance to *Cladosporium fulvum*); Martin et al. (1993) *Science* 262:1432 (tomato Pto gene for resistance to *Pseudomonas syringae* pv. tomato encodes a protein kinase); Mindrinos et al. (1994) *Cell* 78:1089 (Arabidopsis RSP2 gene for resistance to *Pseudomonas syringae*).

*Bacillus thuringiensis* protein, a derivative thereof, or a synthetic polypeptide modeled thereon. (See, for example, Geiser et al. (1986) *Gene* 48:109, who disclose the cloning and nucleotide sequence of a Bt δ-endotoxin gene. Moreover, DNA molecules encoding δ-endotoxin genes can be purchased from American Type Culture Collection (Rockville, Md.), under ATCC Accession Nos. 40098, 67136, 31995, and 31998.

A lectin. See, for example, the disclosure by Van Damme et al. (1994) *Plant Mol. Biol.* 24:825, who disclose the nucleotide sequences of several *Clivia miniata* mannose-binding lectin genes A vitamin-binding protein such as avidin. See U.S. application Ser. No. 07/911,864, the contents of which are hereby incorporated by reference. The application teaches the use of avidin and avidin homologues as larvicides against insect pests.

An enzyme inhibitor, for example, a protease inhibitor or an amylase inhibitor. See, for example, Abe et al. (1987) *J. Biol. Chem.* 262:16793 (nucleotide sequence of rice cysteine proteinase inhibitor); Huub et al. (1993) *Plant Mol. Biol.* 21:985 (nucleotide sequence of cDNA encoding tobacco proteinase inhibitor I); and Sumitani et al. (1993) *Biosci. Biotech. Biochem.* 57:1243 (nucleotide sequence of *Streptomyces nitrosporeus* α-amylase inhibitor).

An insect-specific hormone or pheromone such as an ecdysteroid and juvenile hormone, a variant thereof, a mimetic based thereon, or an antagonist or agonist thereof. See, for example, the disclosure by Hammock et al. (1990) *Nature* 344:458, of baculovirus expression of cloned juvenile hormone esterase, an inactivator of juvenile hormone.

An insect-specific peptide or neuropeptide that, upon expression, disrupts the physiology of the affected pest. See, for example, the disclosures of Regan (1994) *J. Bio. Chem.* 269:9 (expression cloning yields DNA coding for insect diuretic hormone receptor); and Pratt et al. (1989) *Biochem. Biophys. Res. Commun.* 163:1243 (an allostatin is identified in *Diploptera puntata*). See also U.S. Pat. No. 5,266,317, which discloses genes encoding insect-specific, paralytic neurotoxins.

An insect-specific venom produced in nature by a snake, a wasp, etc. For example, see Pang et al. (1992) *Gene* 116:165, for disclosure of heterologous expression in plants of a gene coding for a scorpion insectotoxic peptide.

An enzyme responsible for a hyperaccumulation of a monterpene, a sesquiterpene, a steroid, hydroxamic acid, a phenylpropanoid derivative, or another non-protein molecule with insecticidal activity;

An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT application WO 93/02197, which discloses the nucleotide sequence of a callase gene. DNA molecules that contain chitinase-encoding sequences can be obtained, for example, from the ATCC under Accession Nos. 39637 and 67152. See also Kramer et al. (1993) *Insect Biochem. Mol. Biol.* 23:691, disclosing the nucleotide sequence of a cDNA encoding tobacco hookworm chitinase, and Kawalleck et al. (1993) *Plant Molec. Biol.* 21:673, providing the nucleotide sequence of the parsley ubi4-2 polyubiquitin gene.

A molecule that stimulates signal transduction. For example, see Botella et al. (1994) *Plant Mol. Biol.* 24:757, disclosing nucleotide sequences for mung bean calmodulin cDNA clones, and Griess et al. (1994) *Plant Physiol.* 104: 1467, providing the nucleotide sequence of a maize calmodulin cDNA clone.

A hydrophobic-moment peptide. See U.S. application Ser. No. 08/168,809, which discloses peptide derivatives of Tachyplesin that inhibit fungal plant pathogens, and U.S. application Ser. No. 08/179,632, which teaches synthetic antimicrobial peptides that confer disease resistance.

A membrane permease, a channel former, or a channel blocker. For example, see Jaynes et al. (1993) *Plant Sci.* 89:43, which discloses heterologous expression of a cecropin-β lytic peptide analog to render transgenic tobacco plants resistant to *Pseudomonas solanacearum*.

A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al. (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

An insect-specific antibody or an immunotoxin derived therefrom. Thus, an antibody targeted to a critical metabolic function in the insect gut would inactivate an affected enzyme, killing the insect gut. Cf Taylor et al. (1994) Abstract #497, Seventh International Symposium on Molecular Plant-Microbe Interactions (1994), disclosing enzymatic inactivation in transgenic tobacco via production of single-chain antibody fragments.

A virus-specific antibody. See, for example, Tavladoraki et al. (1993) Nature 366:469, showing that transgenic plants expressing recombinant antibody genes are protected from virus attack.

A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al. (1992) Bio/Technology 10:1436. The cloning and characterization of a gene that encodes a bean endopolygalacturonase-inhibiting protein is described by Toubart et al. (1992) Plant J. 2:367.

A developmental-arrestive protein produced in nature by a plant. For example, Logemann et al. (1992) Bio/Technology 10:305, have shown that transgenic plants expressing the barley ribosome-inactivating gene have an increased resistance to fungal disease.

A herbicide that inhibits the growing point or meristem, such as an imidazalinone or a sulfonylurea. Exemplary genes in this category code for mutant ALS and AHAS enzyme as described, for example, by Lee et al. (1988) EMBO J. 7:241, and Miki et al. (1990) Theor. Appl. Genet. 80:449, respectively.

Glyphosate (resistance imparted by mutant EPSP synthase and aroA genes, respectively) and other phosphono compounds such as glufosinate (PAT and bar genes), and pyridinoxy or phenoxy proprionic acids and cycloshexones (ACCase inhibitor-encoding genes). See, for example, U.S. Pat. No. 4,940,835, which discloses the nucleotide sequence of a form of EPSP that can confer glyphosate resistance. A DNA molecule encoding a mutant aroA gene can be obtained under ATCC Accession No. 39256, and the nucleotide sequence of the mutant gene is disclosed in U.S. Pat. No. 4,769,061. European Patent Application No. 0 333 033 and U.S. Pat. No. 4,975,374 disclose nucleotide sequences of glutamine synthetase genes that confer resistance to herbicides such as L-phosphinothricin. The nucleotide sequence of a phosphinothricin-acetyl-transferase gene is provided in European Patent Application No. 0 242 246. De Greef et al. (1989) Bio/Technology 7:61 describes the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2, and Acc1-S3 genes described by Marshall et al. (1992) Theor. Appl. Genet. 83:435.

A herbicide that inhibits photosynthesis, such as a triazine (psbA and gs+ genes) and a benzonitrile (nitrilase gene). Przibilla et al. (1991) Plant Cell 3:169 describes the transformation of Chlamydomonas with plasmids encoding mutant psbA genes. Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992) Biochem. J. 285:173.

Modified fatty acid metabolism, for example, by transforming a plant with an antisense gene of stearoyl-ACP desaturase to increase stearic acid content of the plant. See Knultzon et al. (1992) Proc. Natl. Acad. Sci. USA 89:2624.

Decreased phytate content. Introduction of a phytase-encoding gene would enhance breakdown of phytate, adding more free phosphate to the transformed plant. For example, see Van Hartingsveldt et al. (1993) Gene 127:87, which discloses the nucleotide sequence of an Aspergillus niger phytase gene. Alternatively, a gene could be introduced that reduces phytate content. In maize, this, for example, could be accomplished, by cloning and then reintroducing DNA associated with the single allele that is responsible for maize mutants characterized by low levels of phytic acid. See Raboy et al. (1990) Maydica 35:383.

Modified carbohydrate composition effected, for example, by transforming plants with a gene coding for an enzyme that alters the branching pattern of starch. See Shiroza et al. (1988) J. Bacteriol. 170:810 (nucleotide sequence of Streptococcus mutans fructosyltransferase gene); Steinmetz et al. (1985) Mol. Gen. Genet. 200:220 (nucleotide sequence of Bacillus subtilis levansucrase gene); Pen et al. (1992) Bio/Technology 10:292 (production of transgenic plants that express Bacillus licheniformis α-amylase); Elliot et al. (1993) Plant Mol. Biol. 21:515 (nucleotide sequences of tomato invertase genes); Søogaard et al. (1993) J. Biol. Chem. 268:22480 (site-directed mutagenesis of barley amylase gene); and Fisher et al. (1993) Plant Physiol. 102:1045 (maize endosperm starch branching enzyme II).

Libraries are preferably constructed from the following genera: Annual broadleaves: velvetleaf (Abutilon theophrasti); pigweed (Amaranthus spp.); buttonweed (Borreria spp.); oilseed rape, canola, indian mustard, etc. (Brassica spp.); comrelina (Commelina spp.); filaree (Erodium spp.); sunflower (Helianthus spp.); morningglory (Ipomoea spp.); kochia (Kochia scoparia); mallow (Malva spp.); wild buckwheat, smartweed, etc. (Polygonum spp.); purslane (Portulaca spp.); russian thistle (Salsola spp.); sida (Sida spp.); wild mustard (Sinapis arvensis); cocklebur (Xanthium spp.). Annual narrowleaves: wild oat (Avena fatua); carpetgrass (Axonopus spp.); downy brome (Bromus tectorurn); crabgrass (Digitaria spp.); barnyardgrass (Echinochloa crusgalli); goosegrass (Eleusine indica); annual ryegrass (Lolium multiflorum); rice (Oryza sativa); ottochloa (Ottochloa nodosa); bahiagrass (Paspalum notatum); canarygrass (Phalaris spp.); foxtail (Setaria spp.); wheat (Triticurn aestivum); corn (Zea mays); Perennial broadleaves: mugwort (Artemisia spp.); milkweed (Asclepias spp.); canada thistle (Cirsium arvense); field bindweed (Convolvulus arvensis); kudzu (Pueraria spp.). Perennial narrowleaves: brachiaria (Brachiaria spp.); bermudagrass (Cynodon dactylon); yellow nutsedge (Cyperus esculentus); purple nutsedge (C. rotundus); quackgrass (Elymus repens); lalang (Imperata cylindrica); perennial ryegrass (Lolium perenne); guineagrass (Panicum maximum); dallisgrass (Paspalum dilatatum); reed (Phragmites spp.); johnson grass (Sorghum halepense); cattail (Typha spp.). Other perennials: horsetail (Equisetum spp.); bracken (Pteridium aquilinum); blackberry (Rubus spp.); gorse (Ulex europaeus).

Also provided by the present invention are seeds comprising at least one polynucleotide herein disclosed. Preferred are those seeds which comprise an expression vector having an operable gene, including many of the functional genes previously described as well as genes that respond to an environmental condition.

Also provided by the present invention are plants that are either transformed or transfected by any of the polynucleotides herein disclosed, or grown from a seed that comprises any of the polynucleotides herein disclosed. Preferably, a plant grown from a seed that comprises a polynucleotide herein conveys in the plant a phenotype different from the phenotype of a plant grown from a genetically-identical seed that does not comprise the polynucleotide. This phenotype can either be as a result of a constitutive expression of a gene, the deletion of a gene, or in response to an environmental cue. Particularly preferred are those plants wherein the phenotype is selected from a group consisting of a: marker gene, disease resistance gene; nutrient-enhancing gene; color-enhancing gene; drought-tolerance gene; rot tolerance gene; ethanol processing-enhancing gene; fungal resistance gene; insect-resistance gene; nematode resistance gene; virus resistance gene; altered carbohydrate composition gene; altered oil composition gene; seed storage proteins with altered amino acid composition gene; male sterility gene; delayed fruit ripening gene; salt resistance gene; herbicide resistance gene; and production of pharmaceutical product gene.

Cells useful in the present invention are any cells, particularly cells which are easily cultured, such as yeast and *E. coli*. However, plant cells useful to harness the recombinatory aspects of the present invention are also preferred, particularly commercial crop plant cells, such as rice, corn, wheat, *sorghum*, barley and any other grain.

Prokaryotic cells are also preferred, particularly for culturing cells useful for herbicide assays herein. Prokaryotes include various strains of *E. coli*; however, other microbial strains may also be used, including, for example, *Bacillus* sp, *Salmonella*, and *Agrobacterium*. Exemplary *Agrobacterium* strains include C58c1 (pGUSINT), Agt121 (pBUSINT), EHA101 (pMTCA23GUSINT), EHA105 (pMT1), LBA4404 (pTOK233), GU2260, BU3600, AGL-1, and LBA4402. Such strains are described in detail in Chan et al. (1992) Plant Cell Physiol 33:577; Smith et al. (1995) Crop Sci 35:301; and Hiei et al. (1994) Plant J 6:271-282. Exemplary bacterial strains include, but are not limited to, C600 (ATCC 23724), C600hfl, DH1 (ATCC 33849), DH5α, DH5αF', ER1727, GM31, GM119 (ATCC 53339), GM2163, HB101 (ATCC 33694), JM83 (ATCC 35607), JM101 (ATCC 33876), JM103 (ATCC 39403), JM1 05 (ATCC 47016), JM107 (ATCC 47014), JM108, JM1 09 (ATCC53323), JM 110 (ATCC 47013), LE392 (ATCC 33572), K802 (ATCC 33526), NM522 (ATCC 47000), RR1 (ATCC31343), X1997 (ATCC 31244), and Y1088 (ATCC 37195). See also, Jendrisak et al. (1987) *Guide to Molecular Cloning Techniques*, Academic Press, 359-371, Hanahan et al. (1983) J Mol Biol 166:557-580, Schatz et al. (1989) Cell 59:1035, Bullock et al. (1987) BioTechniques 5:376-378, ATCC Bacteria and Bacteriophages (1996) 9$^{th}$ Edition, and Palmer et al. (1994) Gene 143:7-8.

As used herein, transformation means processes by which cells/tissues/plants acquire properties encoded on a nucleic acid molecule that has been transferred to the cell/tissue/plant. Transfecting refers to methods to transfer DNA into cells including, but not limited to, microinjection, permeabilizing the cell membrane with various physical (e.g., electroporation) or chemical (e.g., polyethylene glycol, PEG) treatments, high-velocity microprojectile bombardment also termed biolistics, or infection with *Agrobacterium tumefaciens* or *A. rhizogenes*. As used herein, transformant means a plant which has acquired properties encoded on a nucleic acid molecule that has been transferred to cells during the process known as transformation.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

EXAMPLES

Example 1

Construction of Fosmid Library, Sequence Analysis

Genomic DNA was isolated from a susceptible line of the *sorghum* cultivar Colby using the standard CTAB method (M. G. Murray, W. F. Thomson, *Nucl. Acids Res.* 8:4321 (1980)). For fosmid library construction the CopyControl Fosmid Library Production Kit from Epicentre (Madison, Wis., USA) was used by following the manufacturer's instructions. Library screening was carried out using PCR primers specific for the NBS-LRR gene family. These primers were designed using the corresponding genomic region in the *sorghum* line BTx623 as a template, which was sequenced in a previous work of the authors (E. D. Nagy et al., *Theor. Appl. Genet.* (in press)). Four positive clones were found, they were subcloned using the TOPO TA Cloning Kit (Invitrogen, Carlsbad, Calif., USA) and sequenced.

For base calling and sequence assembly, the programs Phred and Phrap were used, respectively (B. Ewing, L. Hillier, M. Wendl, P. Green, *Genome Res.* 8, 175 (1998)). Contigs were visualized and edited with the program CONSED (D. Gordon, C. Abajian, P Green, *Genome Res.* 8, 195 (1998)). Sequence homology searching was performed using the BLAST program package (V. V. Solovyev, A. A. Salamov, *Intel. Syst. Mol. Biol.* 5, 294 (1997)). For gene prediction the program FGENESH (S. F. Altschul, W. Gish, W. Miller, E. W. Myers, D. J. Lipman, *J. Mol. Biol.* 215, 403 (1990)) was applied. The annotation results were edited in the software program Apollo (S. E. Lewis et al., *Genome Biol.* 3, research 0082.1 (2002)).

Four clones covering the NBS-LRR genes were isolated, sequenced and assembled into a single contig of 78,705 bp. Annotation revealed three NBS-LRR gene paralogues (A, B and C), arrayed tandemly in a head-to-tail fashion. The three paralogues are predicted to encode proteins of 1277, 1194 and 1257 amino acids, respectively. The paralogues were separated by respective A-B and B-C intergenic regions of 12,638 and 13,713 bp. The N-terminal and NBS regions (bp 1-1399) were identical in paralogues A and C, while paralogue B was different from the other two across the entire gene. The overall nucleotide similarity was fairly high (over 90%) in all pair-wise comparisons among the three paralogues. Sequencing of RT-PCR products revealed that all three paralogues were transcribed in the seedling roots of uninfected Pc/Pc Colby plants.

Example 2

Analysis of the Gene Configurations in the Pc-Mutant Isogenic Lines

Two primers, Pa11F (GAACATTTCTGCCGCCA-CATTTC) SEQ ID NO:5, and Pa11R (AGCAGTTAGGCGT-TGTATGGATTG) SEQ ID NO:6, common to the termini of all three paralogues were used to amplify the NBS-LRR units in the Pc-mutant isolines. The long-distance (LD) PCR mixture (50 µl) contained 150 ng genomic DNA, 2.5 U Herculase Enhanced DNA polymerase (Stratagene, La Jolla, Calif., USA), 100 ng of each primer and 200 μM of each dNTP. The thermocycling profile was set up according to the instructions provided with the DNA polymerase. The PCR products were isolated from agarose gels using the Qiaex II Gel Extraction Kit (Quiagen, Valencia, Calif., USA) and cloned using the TOPO TA Kit. At least 24 of the clones were sequenced from each genotype to reconstitute their gene configurations. Sequence alignments between the susceptible Colby and Pc-mutant paralogues were performed using ClustalW (D. Higgins et al., *Nucleic Acids Res.* 22, 4673 (1994)). Alignments were viewed and edited with Mega 3.1 (S. Kumar, K. Tamura, M. Nei, *Brief Bioinform* 5, 50 (2004)).

Long-distance PCR was used to amplify the paralogues in the pc-mutant genotypes. Seven of the thirteen mutants (M1-7) contained a single paralogue that was identical with paralogue A in the 5' region, while their 3' end aligned with paralogue C. These are the products of unequal recombination events that occurred between paralogues A and C (FIG. 1). RT-PCR studies indicated that the A/C paralogue is expressed in the seedling roots of all seven mutants.

Three of the mutants (M8-10) exhibited a single paralogue that was indistinguishable from paralogue C. Because A and C paralogues are identical in sequence from bp 1399 within the genes to some 870 bp upstream of the genes, we cannot precisely map where these unequal recombination events occurred. The single NBS-LRR paralogue in these mutants was also found to be expressed by RT-PCR analysis.

Mutant M11 contained intact paralogues A and C, but lacked paralogue B. An unequal recombination event between the A-B and B-C intergenic regions can explain this result. These two intergenic regions are highly similar to each other (76%), including many long (several hundred bp) stretches of identical DNA that would provide ample homology for unequal recombination. RT-PCR analysis demonstrated that paralogues A and C in M11 were also transcribed. Therefore, the only obvious genetic change in M11 was the loss of paralogue B, suggesting that it is the Pc locus.

Mutant M12 was found to contain intact paralogues A and C, and a paralogue B that is truncated by an internal deletion of 468 bp in the LRR region. The deletion breakpoints are flanked by 8 bp-long homologous motifs suggestive of illegitimate recombination (13, 14, 15). All three paralogues in M12 were found to be transcribed. These results demonstrate that internal deletion in paralogue B was sufficient to cause a Pc to pc mutation, thereby proving that paralogue B is the Pc gene.

Mutant M13 carries an intact paralogue A, a recombinant A/C and another B/C paralogue. RT-PCR studies, followed by cloning and sequencing of the PCR products, demonstrated that paralogue A/C in this mutant is transcribed, but paralogues A and B/C are silenced. The observed gene configuration can be explained by a series of consecutive rearrangements including two unequal recombination events. Nevertheless, the lack of a full-length, transcribed paralogue B in M13 is consistent with the finding that paralogue B is responsible for peritoxin susceptibility.

Fourteen rearrangements, 13 unequal recombinations and one deletion, were detected in the 13 Pc to pc mutations (Table 1). Nine of these unequal recombinations were resolved inside a 560 bp segment of the LRR region (bp 3062-3622). This segment was favored for unequal recombinations, in spite of the fact that it is less homologous than the other regions (FIG. 3). The deletion in M12 caused by illegitimate recombination also occurred within this segment, suggesting a double-strand break (19, 20) inside this high-recombination region.

Example 3

Expression Analysis of the NBS-LRR Paralogues

Total RNA was isolated from 2-5 cm radicles of *sorghum* seeds germinated in sterile MS medium on filter paper using the Trisol reagent (Invitrogen). Subsequently, the mRNA fraction was isolated with FastTrack 2.0 mRNA isolation Kit (Invitrogen). For cDNA synthesis the SupersScript III First-Strand Synthesis System (Invitrogen) was used. A primer pair amplifying a 286 bp fragment from paralogue B and a 425 bp fragment from paralogues A and C was used in PCR. The cDNAs and their corresponding negative controls having no reverse transcriptase in the reaction mixture were used as a template. The resulting bands were isolated from the gel and cloned with the TOPO TA Cloning Kit. To have at least one sample from each type of transcripts expressed, at least twenty four clones were sequenced from susceptible Colby and the Pc-mutants carrying multiple NBS-LRR paralogues. Twelve clones were sequenced from mutants containing a single paralogue.

However, in this Pc study, only loss of paralogue B was required to create the Pc to pc phenotype that was selected. Hence, these results indicate a preferential site-direction of the cross-over resolution of recombination events to a small area within an LRR cluster, and one that is particularly low in sequence homology. This phenotype has the earmarks of site-directed recombination, a rare eukaryotic phenomenon not previously observed in plants, but one that has key roles in other eukaryotic kingdoms, including in the creation or escape of a disease resistance response.

TABLE 1

Rearrangement of an NBS-LRR gene family (paralogues A, B and C) detected in pc-mutant isolines. Unequal recombination breakpoints were assigned to intervals flanked by the two closest polymorphic sites between the participating paralogues.

| pc-mutant | Paralogue | Rearrangement | Site of recombination or deletion (intervals in bp)* | Gene expression |
|---|---|---|---|---|
| M1 | A/C | unequal rec. | 3062-3135 | + |
| M2 | A/C | unequal rec. | 3162-3220 | + |
| M3 | A/C | unequal rec. | 3258-3312 | + |
| M4 | A/C | unequal rec. | 3258-3312 | + |
| M5 | A/C | unequal rec. | 3312-3380 | + |
| M6 | A/C | unequal rec. | 3312-3380 | + |

TABLE 1-continued Rearrangement of an NBS-LRR gene family (paralogues A, B and C) detected in pc-mutant isolines. Unequal recombination breakpoints were assigned to intervals flanked by the two closest polymorphic sites between the participating paralogues.

| pc-mutant | Paralogue | Rearrangement | Site of recombination or deletion (intervals in bp)* | Gene expression |
|---|---|---|---|---|
| M7 | A/C | unequal rec. | 3473-3521 | + |
| M8 | C | unequal rec. | intergenic or 1-1499 | + |
| M9 | C | unequal rec. | intergenic or 1-1499 | + |
| M10 | C | unequal rec. | intergenic or 1-1499 | + |
| M11 | A | unequal rec. | intergenic | + |
|  | C | unequal rec. | intergenic | + |
| M12 | A | — | — | + |
|  | Bdel | deletion | 2764-3231 | + |
|  | C | — | — | + |
| M13 | A | — | — | − |
|  | A/C | unequal rec. | 3312-3380 | + |
|  | B/C | unequal rec. | 3425-3622 | − |

*as localized in a 3737 bp consensus sequence of paralogues A, B and C

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

We claim:

1. A system for identifying a genetic sequence in a plant associated with toxin resistance in the plant, comprising:
   providing an isolated polynucleotide comprising SEQ ID NO:1;
   providing a genetic sample of the plant;
   analyzing the sample for the presence of a first nucleic acid sequence having at least 95% identity to SEQ ID NO:1; and analyzing the first nucleic acid sequence for the presence or absence of a second nucleic acid sequence comprising at least 95% sequence identity to bases 3061-3621 of SEQ ID NO:1, wherein the absence of the second nucleic acid sequence is indicative of toxin resistance in the plant.

2. The system of claim 1, wherein the toxin resistance is resistance to *Periconia peritoxin*.

3. The system of claim 1, wherein the plant is a monocot.

4. The system of claim 1, wherein the plant is one selected from the group consisting of: corn (*Zea mays*), a *Brassica* sp., *Brassica napus, Brassica rapa, Brassica juncea*, alfalfa (*Medicago saliva*), rice (*Oryza sativa*), rye (*Secale cereale*), a *sorghum, Sorghum bicolor, Sorghum vulgare*, a millet, pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense*), *Gossypium hirsutum*, sweet potato (*Ipomoea batatus*), cassava (*Manihot esculenta*), a coffee plant (*Coffea* spp.), coconut (*Cocos nucifera*), pineapple (*Ananas comosus*), a citrus plant (*Citrus* spp.), cocoa (*Theobroma cacao*), tea (*Camellia sinensis*), a banana plant (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), an oat plant (*Avena* spp.), a barley plant (*Hordeum* spp.), palm, a legume, beans, peas, guar, locust bean, fenugreek, garden bean, cowpea, mungbean, lima bean, fava bean, lentil, chickpea, castor, *Arabidopsis*, a vegetable, an ornamental, a grass, a conifer, a crop plant that provides seeds of interest, a grain plant that provides seeds of interest, an oil-seed plant, a leguminous plant, tomato (*Lycopersicon esculentum*), lettuce, *Lactuca sativa*, green beans (*Phaseolus vulgaris*), lima beans (*Phaseolus limensis*), peas (*Lathyrus* spp.), a member of the genus *Cucumis*, cucumber (*Cucumis sativus*), cantaloupe (*Cucumis cantalupensis*), musk melon (*Cucumis melo*), an azalea (*Rhododendron* spp.), hydrangea (*Macrophylla hydrangea*), hibiscus (*Hibiscus rosasanensis*), a rose plant (*Rosa* spp.), a tulip plant (*Tulipa* spp.), a daffodil plant (*Narcissus* spp.), petunia (*Petunia hybrida*), carnation (*Dianthus caryophyllus*), poinsettia (*Euphorbia pulcherrima*), chrysanthemum, a pine tree, loblolly pine (*Pinus taeda*), slash pine (*Pinus elliotil*), ponderosa pine (*Pinus ponderosa*), lodgepole pine (*Pinus contorta*), Monterey pine (*Pinus radiata*), Douglas-fir (*Pseudotsuga menziesil*), Western hemlock (*Tsuga canadensis*), Sitka spruce (*Picea glauca*), redwood (*Sequoia sempervirens*), a true fir tree, silver fir (*Abies amabilis*), balsam fir (*Abies balsamea*), a cedar tree, Western red cedar (*Thuja plicata*) and Alaska yellow-cedar (*Chamaecyparis nootkatensis*).

5. The system of claim 1, wherein the genetic sample is analyzed for a sequence having at least 95% identity to SEQ ID NO: 1 by BLAST algorithm.

6. The system of claim 1, wherein the genetic sample is analyzed for a sequence having at least 97% identity to SEQ ID NO:1.

7. A method for identifying a genetic sequence in a plant associated with toxin resistance in the plant, comprising:

providing an isolated polynucleotide comprising SEQ ID NO:1;

providing a genetic sample of the plant;

analyzing the sample to identify a first nucleic acid sequence having at least 95% identity to SEQ ID NO: 1; and analyzing the first nucleic acid sequence to identify the presence or absence of a second nucleic acid sequence comprising at least 95% sequence identity to bases 3061-3621 of SEQ ID NO:1, wherein the identification of the absence of the second nucleic acid sequence is indicative of toxin resistance in the plant.

8. The method of claim 7, wherein the toxin resistance is resistance to *Periconia* peritoxin.

9. The method of claim 7, wherein the plant is a monocot.

10. The method of claim 7, wherein the plant is one selected from the group consisting of: corn (*Zea mays*), a *Brassica* sp., *Brassica napus, Brassica rapa, Brassica juncea*, alfalfa (*Medicago sativa*), rice (*Oryza sativa*), rye (*Secale cereale*), a sorghum, *Sorghum bicolor, Sorghum vulgare*, a millet, pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense*), *Gossypium hirsutum*, sweet potato (*Ipomoea batatus*), cassava (*Manihot esculenta*), a coffee plant (*Coffea* spp.), coconut (*Cocos nucifera*), pineapple (*Ananas comosus*), a citrus plant (*Citrus* spp.), cocoa (*Theobroma cacao*), tea (*Camellia sinensis*), a banana plant (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), an oat plant (*Avena* spp.), a barley plant (*Hordeum* spp.), palm, a legume, beans, peas, guar, locust bean, fenugreek, garden bean, cowpea, mungbean, lima bean, fava bean, lentil, chickpea, castor, *Arabidopsis*, a vegetable, an ornamental, a grass, a conifer, a crop plant that provides seeds of interest, a grain plant that provides seeds of interest, an oil-seed plant, a leguminous plant, tomato (*Lycopersicon esculentum*), lettuce, *Lactuca sativa*, green beans (*Phaseolus vulgaris*), lima beans (*Phaseolus limensis*), peas (*Lathyrus* spp.), a member of the genus *Cucumis*, cucumber (*Cucumis sativus*), cantaloupe (*Cucumis cantalupensis*), musk melon (*Cucumis melo*), an azalea (*Rhododendron* spp.), hydrangea (*Macrophylla hydrangea*), hibiscus (*Hibiscus rosasanensis*), a rose plant (*Rosa* spp.), a tulip plant (*Tulipa* spp.), a daffodil plant (*Narcissus* spp.), petunia (*Petunia hybrida*), carnation (*Dianthus caryophyllus*), poinsettia (*Euphorbia pulcherrima*), chrysanthemum, a pine tree, loblolly pine (*Pinus taeda*), slash pine (*Pinus elliotil*), ponderosa pine (*Pinus ponderosa*), lodgepole pine (*Pinus contorta*), Monterey pine (*Pinus radiata*), Douglas-fir (*Pseudotsuga menziesil*), Western hemlock (*Tsuga canadensis*), Sitka spruce (*Picea glauca*), redwood (*Sequoia sempervirens*), a true fir tree, silver fir (*Abies amabilis*), balsam fir (*Abies balsamea*), a cedar tree, Western red cedar (*Thuja plicata*) and Alaska yellow-cedar (*Chamaecyparis nootkatensis*).

11. The method of claim 7, wherein the genetic sample is analyzed for a sequence having at least 95% identity to SEQ ID NO:1 by BLAST algorithm.

12. The method of claim 7, wherein the genetic sample is analyzed for a sequence having at least 97% identity to SEQ ID NO:1.

13. An isolated polynucleotide selected from the group consisting of: SEQ ID NO:2; SEQ ID NO:3; SEQ ID NO:4; SEQ ID NO:5; and SEQ ID NO:6.

14. An isolated polynucleotide comprising at least 95% sequence identity to bases 3061-3621 of SEQ ID NO:1.

15. The isolated polynucleotide of claim 14, comprising at least 97% sequence identity of said bases.

16. An isolated polynucleotide comprising at least 95% identity with the polynucleotide of SEQ ID NO: 1.

17. The polynucleotide of claim 16, wherein said polynucleotide comprises at least 97% sequence identity to said SEQ ID NO:1.

18. A method to identify if a test compound interacts with an expression product of the polynucleotide of claim 16, the method comprising contacting the test compound with the expression product and determining whether the test compound interacts with said expression product.

* * * * *

UNITED STATES PATENT AND TRADEMARK OFFICE
CERTIFICATE OF CORRECTION

PATENT NO.       : 8,445,746 B2                                    Page 1 of 1
APPLICATION NO.  : 12/528290
DATED            : May 21, 2013
INVENTOR(S)      : Bennetzen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 679 days.

Signed and Sealed this
Eighth Day of September, 2015

Michelle K. Lee
*Director of the United States Patent and Trademark Office*